United States Patent
Selvaraj et al.

(10) Patent No.: US 11,062,804 B2
(45) Date of Patent: Jul. 13, 2021

(54) SYNTHETIC SIMULATION SYSTEM FOR TESTING OF PHYSIOLOGICAL MONITORING DEVICES

(71) Applicant: Vital Connect, Inc., San Jose, CA (US)

(72) Inventors: Nandakumar Selvaraj, San Jose, CA (US); Paul Kettle, San Jose, CA (US)

(73) Assignee: VITAL CONNECT, INC., San Jose, CA (US)

( * ) Notice: Subject to any disclaimer, the term of this patent is extended or adjusted under 35 U.S.C. 154(b) by 342 days.

(21) Appl. No.: 16/123,260

(22) Filed: Sep. 6, 2018

(65) Prior Publication Data

US 2019/0272916 A1 Sep. 5, 2019

Related U.S. Application Data

(60) Provisional application No. 62/631,624, filed on Feb. 16, 2018.

(51) Int. Cl.
*G06F 11/30* (2006.01)
*G16H 40/40* (2018.01)

(52) U.S. Cl.
CPC ................. *G16H 40/40* (2018.01)

(58) Field of Classification Search
CPC ..................................... G16H 40/40
See application file for complete search history.

(56) References Cited

U.S. PATENT DOCUMENTS

2015/0038869 A1* 2/2015 Simon .................. A61B 5/0006 600/544
2017/0049400 A1* 2/2017 Falk ..................... A61B 5/7203

* cited by examiner

*Primary Examiner* — Phuong Huynh
(74) *Attorney, Agent, or Firm* — Brundidge & Stanger, P.C.

(57) ABSTRACT

System and method for validating algorithms used in medical devices is disclosed. As disclosed, the system and method include generating a synthetic waveform, inputting the generated synthetic waveform to the testing device, capturing an output values for the input values generating synthetic waveform from the testing device; and comparing the output values to the input values to determine performance metrics of the testing device to validate the algorithm on the testing device.

15 Claims, 4 Drawing Sheets

SYNTHETIC SIMULATION SYSTEM FOR TESTING OF PHYSIOLOGICAL MONITORING DEVICES

CROSS-REFERENCE TO RELATED APPLICATIONS

This application claims the benefit of U.S. Provisional Patent Application No. 62/631,624, filed on Feb. 16, 2018, entitled "SYNTHETIC SIMULATION SYSTEM FOR TESTING OF PHYSIOLOGICAL MONITORING DEVICES," which is incorporated herein by reference in its entirety.

FIELD OF THE INVENTION

The present invention relates to medical devices, and more particularly, to a validation of medical devices and the algorithms used by such devices.

BACKGROUND

Proper validation of algorithms is an on-going technical challenge due to the ever-increasing complexity of the algorithms involved and the environments in which they operate. These challenges are acute for medical applications and overcoming such challenges is paramount for regulatory medical devices in particular.

Moreover, accurate assessment of vital signs and timely notification of critical events are necessary for continuous patient monitoring that can help to detect infections or complications well in advance and prevent mortalities. Recent advancements in wearable medical technologies for 24-hour health monitoring may allow early detection of patient deterioration and curb healthcare costs. The accuracy and precision of algorithms implemented in such complex embedded medical systems are paramount to earn the acceptance of clinical community; therefore, it is very important to ensure high quality of algorithmic design via rigorous testing and validation during the developmental cycles.

Therefore, there is a strong need for a solution that overcomes the aforementioned issues. The present invention addresses such a need.

SUMMARY OF THE INVENTION

Proper validation of algorithms is paramount particularly for regulatory medical devices applied for patient monitoring. Disclosed herein is a novel simulation platform for validation of various algorithms, including continuous respiratory monitoring via a patch medical device. Single-lead ECG and triaxial body acceleration signals with variability and noise are synthetically generated and quantized for a constellation according to the input parameters of heart rate (HR) as a fundamental frequency (fc) of ECG and reference BR as a modulating frequency (fr). Synthetic signals are input to the BR algorithms and the performance of output BRs are evaluated for a region-of-interest of the constellation (fc/fr≥3 & fc/fr≤8) accounting the Nyquist and physiological variability. The proposed simulation platform is efficient for validation of continuous respiratory monitoring and can be applicable for testing other physiological monitoring devices with modular modifications.

BRIEF DESCRIPTION OF THE DRAWINGS

The accompanying figures illustrate several embodiments of the invention and, together with the description, serve to explain the principles of the invention. One of ordinary skill in the art readily recognizes that the embodiments illustrated in the figures are merely exemplary, and are not intended to limit the scope of the present invention.

DETAILED DESCRIPTION

Development of intelligent and efficient algorithms particularly for physiological monitoring and critical event detection necessitates a wide distribution of data belonging to both normal and abnormal conditions. However, obtaining a comprehensive continuous medical-grade data from patients is limited during in-house development and for the validation of algorithms. Moreover, gold-standard reference monitors required for clinical validation of emerging wearable technologies are, in many cases, not designed for ambulatory monitoring. Thus, a synthetic simulator system may be useful to overcome many of those limitations.

The present invention relates to a novel system and method for simulation and validation of medical devices and functions provided by such devices, including continuous respiratory monitoring via a patch medical device that involves synthetic generation and quantization of single-lead ECG and triaxial body acceleration signals with variability and noise for a constellation of input fundamental and modulating frequencies. For example, as disclosed herein, synthetic signals are input to the breathing rate (BR) algorithms of patch sensor, and the performance of output BRs are evaluated for a predefined region-of-interest of the constellation accounting the Nyquist and physiological variability.

Such synthetic simulation system may help to generate surrogate data for early stages of algorithmic design, optimization of the development and test the reliability over a wide range of a target measurement. The system may allow generating synthetic signals, inputting into sensor hardware and firmware algorithms and evaluating performance for a constellation of input variables. Thus, the system may allow assessment of the device performance in not only in common operating ranges but also in uncommon corner cases.

Accordingly, the following description, attached figures and appendices are presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

To describe the features of the present invention in more detail, refer now to the following description in conjunction with the accompanying Figures.

Figure 1:
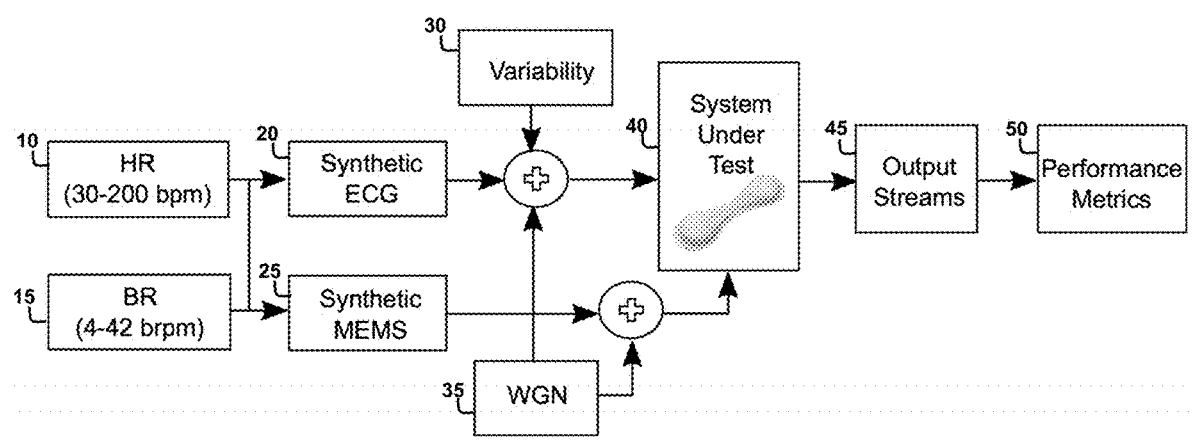
FIG. 1 illustrates a system comprising a synthetic simulation system in accordance with an embodiment.

FIG. 1 illustrates a synthetic simulation system forming a synthetic simulation environment in accordance with an embodiment. According to one of the embodiments disclosed herein, the simulation synthetic system generates and supplies simulated signals for the simulation and validation of a medical device and functions provided by the medical device. According to the present invention the medical device could, for example, include a disposable adhesive patch sensor (e.g., System Under Test 40) worn on chest with built-in system-on-chip processor, and associated electronics that allows continuous monitoring of single-lead ECG, tri-axial accelerometer, and thermistor data using sensors and algorithms that aid in the production of output signals that faithfully and accurately correspond to physiological conditions of the patient being monitored.

The firmware algorithms of the synthetic simulation system computes and continuously transmits signals including one or more of physiologic variables such as heart rate (HR; e.g., HR 10), Breathing Rate (BR; e.g., BR 15), skin temperature (not shown in FIG. 1), body posture (not shown in FIG. 1), fall detection (not shown in FIG. 1), and step count (not shown in FIG. 1), among others. ECG derived R wave amplitude (RWA), measuring change of cardiac axis during breathing, triaxial accelerometer signals, measuring chest wall movements of expansion and compression due to respiratory cycles, and ECG derived respiratory sinus arrhythmia (RSA), measuring respiratory modulations are combined to assess BR values.

For a wide range of HR (30-200 bpm) and BR (4-42 brpm) as input parameters of fundamental ($f_c$) and modulating ($f_r$) frequencies respectively, a single-lead ECG and tri-axial accelerometer waveforms are synthetically generated by Synthetic ECG generator 20 and Synthetic MEMS generator 25, respectively for each combination of HR and BR inputs (e.g., HR 60 and BR 15) as shown in FIG. 1. Variances can, for example, be added to the synthetic waveforms output from the Synthetic ECG generator 20 by Variability Unit 30, which can take any form for varying a signal as known to those of ordinary skill in the art. Also, white Gaussian noise can be added to the synthetic waveforms output from the Synthetic ECG generator 20 as well as to the synthetic waveforms output from the Synthetic MEMS generator 25 by White Gaussian Noise (WGN) Generator 35, which can take any form for generating white Gaussian noise as known to those of ordinary skill in the art. These synthetic waveforms are input to the System Under Test 40, which as described above could, for example, include a disposable adhesive patch sensor. In response to the synthetic waveforms the System Under Test 40 produces based on the patch sensors algorithms BR outputs (e.g., Output 45) that are compared with reference BR values as well as other values by Performance Metrics unit 50 to conduct validation of the System Under Test 40 and functions provided by said system. The performance Metrics unit 50 may include performing error analysis to quantify mean absolute error, mean square error, standard deviation of error, mean error (or bias), limits of agreement, or any other statistical measures of error distribution.

Generation of synthetic ECG signals: A typical ECG waveform is a tracing of changes in electrical depolarization and repolarization of atrial and ventricle muscles of heart and associated time delays. An ECG is composed of a P wave, a QRS complex wave and a T wave, where P wave and QRS complex are depolarization waves and refer to the electrical potentials produced due to atrial depolarization and ventricular depolarization, respectively. Whereas the T wave is a repolarization wave that is produced by the electrical potential associated with the recovery from the depolarization state. The QRS complex is usually further split into separate Q wave, R wave and S wave. The ECG waveform characteristics including wave amplitudes and time durations are known to those of ordinary skill in the art.

A synthetic ECG waveform (e.g., Synthetic ECG 20) can be composed of PQRST, 5 individual waves (P-Q-R-S-T waves) for normal sinus rhythm. Accordingly, the decoupled ECG representation can be approximated by the sum of five Gaussian kernels, where each kernel is described by their amplitude, width, central location and HR (a, σ, μ and ωn respectively). According to one embodiment, a synthetic model used by the system shown in FIG. 1 as described in Equation (1) below includes a scaling factor that transposes dimension-less ECG representation z to mV/(rad×s), and provides QRS amplitude and respiratory sinus arrhythmia (RSA) modulations.

$$z(t) = \sum_{i=1}^{n} \frac{w_n \times a_i}{\sigma_i^2} e^{-\frac{(t-\mu_i)^2}{2\sigma_i^2}} \qquad (1)$$

To mimic clinical data, it is essential to add stochastic variability and noise to the synthetic ECG signals. To this end, a random variability is first added to both the amplitude and frequency modulation of ECG for each HR-BR combinations of the constellation. Further, white Gaussian noise of zero-mean and standard deviation of SDwgn is also added to the ECG as in Equation (2):

$$SD_{wgn} = f_{wgn} \times \sqrt{\frac{1}{(n-1)}\sum_{i=1}^{n}(z_i - \mu)^2} \qquad (2)$$

where, n is the number of samples, and $f_{wgn}$ is a factor (e.g., 0.1). The ECG signal with added noise is further quantized.

Figure 2A:
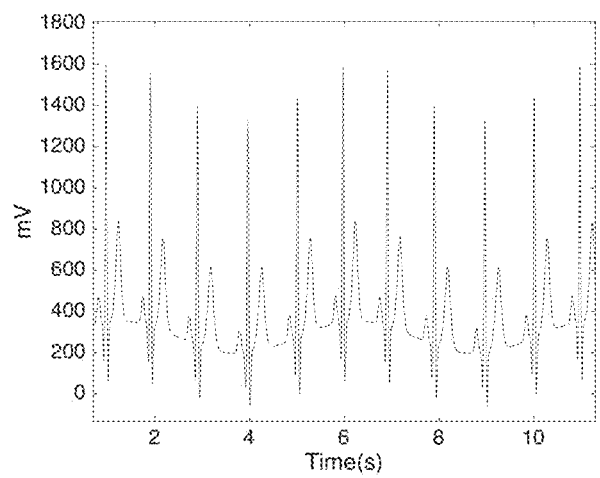
FIGS. 2A and 2B is representative synthetic ECG waveforms (i) without noise and (ii) with stochastic noise.
Figure 2B:
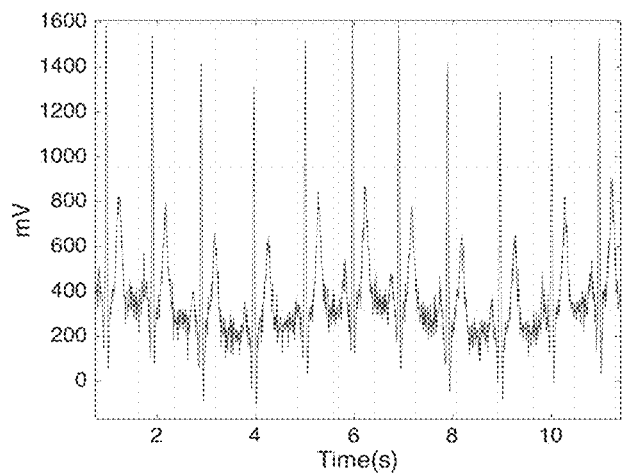

FIG. 2A shows a sample ECG waveform output from synthetic ECG 20 containing the physiological variability driven by a HR of 60 bpm as a fundamental frequency (fc) and a BR of 10 brpm as a modulating frequency (fr), and does not contain any additive randomness and noise. The synthetic ECG waveform output from synthetic ECG 20 (as above) is first added with randomness to their amplitude and frequency modulations using a normally distributed random numbers with a mean and standard deviation such as 1 and 0.3, respectively. This ECG signal further added with white gaussian noise with zero mean and power of, for example, 0.1 standard deviation of ECG signal. FIG. 2B shows the above sample ECG waveform corrupted with stochastic variability and noise.

According to one embodiment disclosed herein, synthetic MEMS signals (e.g., Synthetic MEMS 25) may be generated as follows: the tri-axial accelerometer housed in the printed circuit board of the patch sensor allows capturing human body accelerations. In one example, the specifications of MEMS include a range of ±4 g per axis with a resolution 7.8 mg, where g=9.81 m/s$^2$ is the gravitational acceleration. The acceleration signals are calibrated to rotate the coordinate system and obtain the true superior-inferior, anterior-posterior, and left-right acceleration axes. The chest wall movements caused by respiration are captured by the tri-axial accelerometer, and a MEMS based surrogate respiratory signal is generated for BR estimation. In this simulation environment, tri-axial MEMS signals are synthesized according to the input BR (e.g., BR 15). The MEMS signal (e.g., Synthetic MEMS 25) with added noise (e.g., WGN 35) is further quantized. The synthetic ECG and MEMS signals (e.g., Synthetic ECG 20 and Synthetic MEMS 25) are generated for a predefined time duration such as 180 s with all combinations of HR-BR range, and input to the System Under Test 40 and BR estimates are obtained as shown in FIG. 1.

Figure 3:
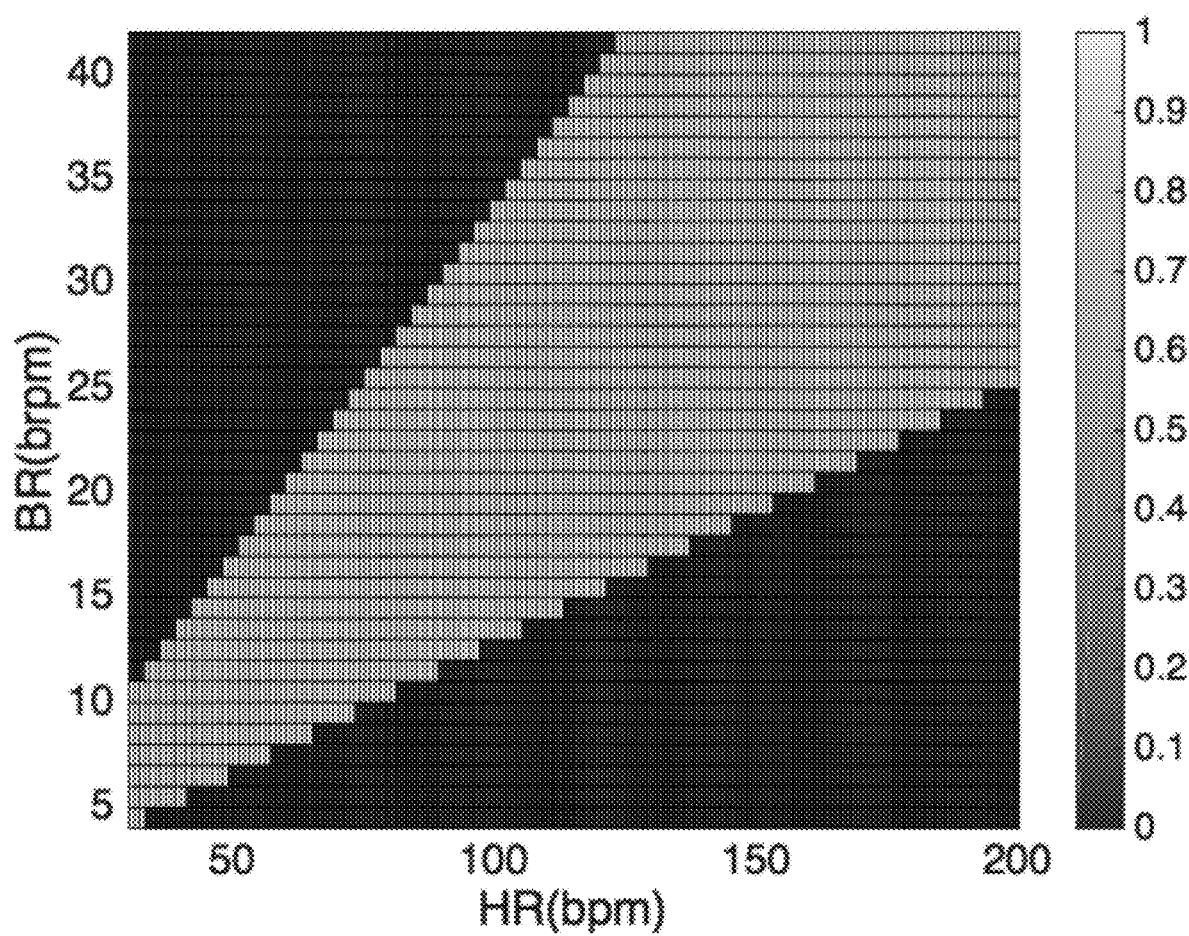
FIG. 3 illustrates the colormap of sample HR-BR constellation points with the R values [0,1] indicating the region-of-interest in accordance with an embodiment described herein.

Region-of-interest (ROI) of the constellation: BR is usually approximated as a linear or piecewise linear function of HR. According to one embodiment, the considered region of interest in the constellation is denoted as R and shown, for example, by a function given in Equation (3), where the ratio of fundamental HR frequency ($f_c$) to the modulating BR frequency ($f_r$) would satisfy the Nyquist criterion to ensure free from cardiac aliasing. The lower bound threshold (R=3) is chosen to satisfy Nyquist rate and the upper bound threshold (R=8) is chosen to account for a limited physiological variability. The constellation points on the ROI with R=1 in the 2D map is shown in FIG. 3 for the input range of HR and BR. This ROI can be further split into 3 sub-regions of low or shallow range (4-9 brpm), clinical range (10-30 brpm) and higher hyperventilation range (31-42 brpm) for performance assessment for these specific regions.

$$R = \begin{cases} 0 & \frac{f_c}{f_r} < 3 \\ 1 & \frac{f_c}{f_r} \geq 3 \ \& \ \frac{f_c}{f_r} \leq 8 \\ 0 & \frac{f_c}{f_r} \geq 3 \end{cases} \quad (3)$$

Figure 4:
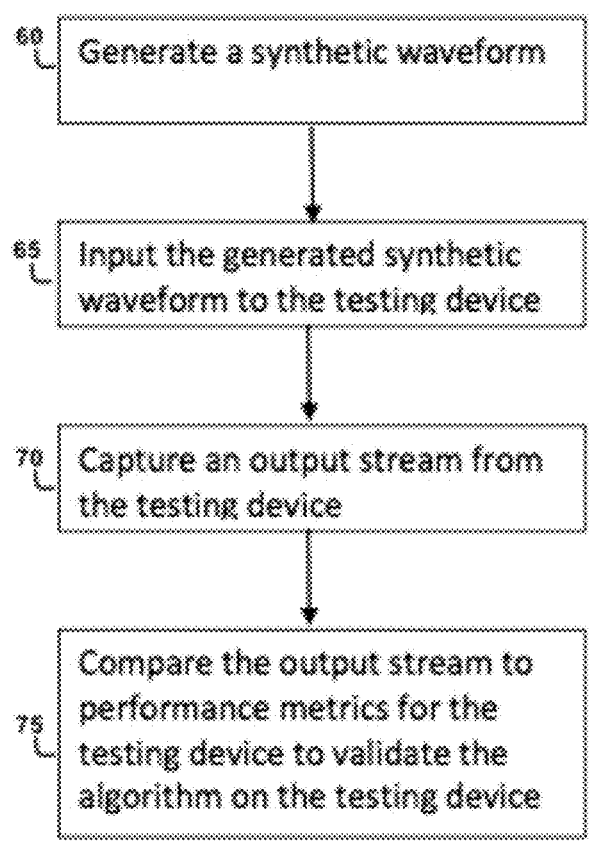
FIG. 4 is a flow diagram illustrating a method in accordance with an embodiment described herein.

FIG. 4 illustrates a method for validating an algorithm on a testing device. As shown, the method includes generating a synthetic waveform at step 60, inputting the generated synthetic waveform to the testing device at step 65, capturing an output stream from the testing device at step 70. Finally, in step 75, the method of FIG. 4 compares the output stream to performance metrics for the testing device to validate the algorithm on the testing device to determine performance metrics using the output stream and thereby validates the algorithm on the testing device.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

The clinical trial data is often limited in capturing wide range of physiological responses such as BR. Thus, the proposed simulation platform may be useful for validation of wearable sensor algorithms to test outside ranges from clinical studies. This simulation platform mimics the use-case of a patient monitoring system with ECG and MEMS sensing for BR assessment by producing input synthetic waveforms for a constellation of underlying control parameters and noise level. Changes in acceleration magnitudes in different axes during different levels of activity and posture simulations can be included into the simulation inputs based on data learning from controlled experiments. Thus, the simulation system can be further modified to mimic more realistic data that may allow planning the development and validation phases of algorithmic designs for physiological monitoring. The simulation environment may enhance rapid prototyping by testing the system performances without requiring to commit laborious clinical studies that may lower the developmental cycles and reduce the time-to-market significantly.

The simulation system can be useful for validation of physiological measurement such as BR and allows modular modifications for incorporating new signal modalities/functionalities that can be applicable for testing other physiological monitoring devices.

What is claimed is:

1. A method for validating an algorithm on a testing device, the method comprising:
   generating at least one synthetic waveform from at least two input values;
   inputting the generated at least one synthetic waveform to the testing device;
   capturing output values from the testing device; and
   comparing the output values to the at least two input values generating the at least one synthetic waveform to determine performance metrics of the testing device to validate the algorithm on the testing device,
   wherein the performance output metrics comprise of statistical measures of error distribution including bias, variance of 95% limits of agreement.

2. The method of claim 1, wherein the generating the at least one synthetic waveform includes adding a random variability and noise.

3. The method of claim 1, wherein a synthetic model is used in the generating the at least one synthetic waveform.

4. The method of claim 3, wherein the synthetic model includes generating a synthetic Electrocardiography (ECG) waveforms and applying at least one of a scaling factor, random variability and random noise for synthetic ECG waveforms.

5. The method of claim 4, wherein the scaling factor transposes a dimensionless ECG representation z to mV/(rad×s).

6. The method of claim 3, wherein the synthetic model includes generating synthetic triaxial accelerometer waveforms of the testing device comprises a tri-axial accelerometer and applying a random noise and random variability to the synthetic acceleration waveforms.

7. A method for validating an algorithm on a testing device, the method comprising:
   generating at least one synthetic waveform from at least two input values, wherein a synthetic model is used in the generating the at least one synthetic waveform;
   inputting the generated at least one synthetic: waveform to the testing device;
   capturing output values from the testing device;
   comparing the output values to the at least two input values generating the at least one synthetic waveform to determine performance metrics of the testing device to validate the algorithm on the testing device; and
   generating a synthetic waveform for a constellation of all combinations of input parameters fundamental frequency and modulating frequency.

8. The method of claim 1, wherein the comparing the output values to the at least two input values generating the at least one synthetic waveform comprises selecting a region of interest in the input constellation of parameters based on a ratio of at least two input independent frequencies, including fundamental frequency fc and modulating frequency fr.

9. A system for validating an algorithm, the system comprising:
   a testing device; and
   a simulation platform, comprising:

generating at least one synthetic waveform from at least two input values;

inputting the at least one generated synthetic waveform to the testing device;

capturing output values from the testing device; and comparing the output values to the at least two input values generating the at least one synthetic waveform to determine performance metrics for the testing device to validate the algorithm on the testing device, wherein a synthetic model is used in generating the at least one synthetic waveform, wherein the synthetic model includes generating synthetic ECG waveforms and applying at least one of a scaling factor, random variability and random noise for synthetic Electrocardiography (ECG) waveforms, and wherein the scaling factor transposes a dimensionless ECG representation z to mV/(rad×s).

10. The system of claim 9, wherein the at least one generating a synthetic waveform includes adding a random variable.

11. The system of claim 9, wherein the synthetic model includes generating synthetic triaxial accelerometer waveforms of a testing device comprises a tri-axial accelerometer and applying a random noise and random variability to the synthetic acceleration waveforms.

12. The system of claim 9, comprising generating synthetic waveform for a constellation of all combinations of input parameters such as fundamental frequency and modulating frequency.

13. The system of claim 9, wherein the comparing the output values to the at least wo input values generating the at least one synthetic waveform comprises selecting R, a region of interest in the input constellation of parameters based on a ratio of at least two input independent frequencies, including fundamental frequency fc and modulating frequency fr.

14. A computer program product stored on a non-transitory computer readable medium, comprising computer readable programming for causing a computer to control an execution of an application for validating an algorithm on a testing device comprising:

generating at least one synthetic waveform from at least two input values;

inputting the generated at least one synthetic waveform to the testing device;

capturing output values from the testing device; and comparing the output values to the at least two input values generating the at least one synthetic waveform to determine performance metrics of the testing device to validate the algorithm on the testing device, wherein the comparing the output values to the at least two input values generating the at least one synthetic waveform comprises selecting R, a region of interest in the in input constellation of parameters based on a ratio of at least two input independent frequencies, including fundamental frequency fc and modulating frequency fr.

15. The computer program product of claim 14, wherein the generating the at least one synthetic waveform includes adding at least one of a scaling factor, random variability and noise.

* * * * *